United States Patent
Kim et al.

(10) Patent No.: US 10,679,079 B2
(45) Date of Patent: Jun. 9, 2020

(54) DRIVER STATE MONITORING METHOD AND APPARATUS

(71) Applicant: Mando-Hella Electronics Corporation, Incheon (KR)

(72) Inventors: Beom-Kyu Kim, Incheon (KR); Ha-Bit Park, Incheon (KR); Ki-Man Kim, Gyeonggi-do (KR); Shinwook Kim, Seoul (KR)

(73) Assignee: MANDO-HELLA ELECTRONICS CORPORATION, Incheon (KR)

( * ) Notice: Subject to any disclaimer, the term of this patent is extended or adjusted under 35 U.S.C. 154(b) by 0 days.

(21) Appl. No.: 15/820,308

(22) Filed: Nov. 21, 2017

(65) Prior Publication Data
US 2018/0260642 A1    Sep. 13, 2018

(30) Foreign Application Priority Data

Mar. 10, 2017 (KR) .................. 10-2017-0030487

(51) Int. Cl.
*G06K 9/00* (2006.01)
*B60Q 9/00* (2006.01)
(Continued)

(52) U.S. Cl.
CPC ........ *G06K 9/00845* (2013.01); *A61B 5/0077* (2013.01); *A61B 5/02444* (2013.01);
(Continued)

(58) Field of Classification Search
CPC ..... G06K 9/00845; G06K 9/6288; A61B 5/18
See application file for complete search history.

(56) References Cited

U.S. PATENT DOCUMENTS

| | | | |
|---|---|---|---|
| 9,135,803 B1 * | 9/2015 | Fields ................. | B60K 28/066 |
| 2011/0169625 A1 * | 7/2011 | James ................... | B60Q 9/008 |
| | | | 340/439 |

(Continued)

FOREIGN PATENT DOCUMENTS

| | | | | |
|---|---|---|---|---|
| EP | 1441528 A1 * | 7/2004 | ............... | B60R 1/00 |
| KR | 10-2015-0068694 | 6/2015 | | |

(Continued)

OTHER PUBLICATIONS

Office Action dated Apr. 2, 2018 for Korean Application No. 10-2017-0030487 and its English machine translation by Google Translate.

*Primary Examiner* — Mainul Hasan
(74) *Attorney, Agent, or Firm* — Ladas & Parry, LLP

(57) ABSTRACT

A driver state monitoring method and apparatus may accurately and effectively determine a driver carelessness state and warn a driver of the carelessness state. The driver state monitoring apparatus includes a driver state sensing unit to sense a driver state; a vehicle state sensing unit to sense a vehicle state, an ambient environment state sensing unit to sense an ambient environment state of the vehicle, a warning unit to warn a driver of a driver carelessness state, and a controller to assign a weighted value to the driver state sensed through the driver state sensing unit and the vehicle state sensed through the vehicle state sensing unit, respectively, based on an ambient environment state sensed through the ambient environment state sensing unit, calculate a driver carelessness level by applying the assigned respective weighted values, determine whether the driver is in a carelessness state or a normal state based on the calculated driver carelessness level, and warn the driver through the warning unit if the driver is in the carelessness state.

5 Claims, 4 Drawing Sheets

(51) Int. Cl.
  *G06K 9/20* (2006.01)
  *G06K 9/62* (2006.01)
  *G01S 13/88* (2006.01)
  *G01S 13/86* (2006.01)
  *A61B 5/024* (2006.01)
  *A61B 5/18* (2006.01)
  *A61B 5/00* (2006.01)
  *G01S 13/931* (2020.01)

(52) U.S. Cl.
  CPC .............. *A61B 5/18* (2013.01); *A61B 5/6893* (2013.01); *B60Q 9/00* (2013.01); *G01S 13/867* (2013.01); *G01S 13/88* (2013.01); *G06K 9/00791* (2013.01); *G06K 9/209* (2013.01); *G06K 9/6288* (2013.01); *G01S 2013/9322* (2020.01)

(56) References Cited

U.S. PATENT DOCUMENTS

| | | | | |
|---|---|---|---|---|
| 2012/0083974 | A1* | 4/2012 | Sandblom | G01S 13/931 701/45 |
| 2014/0139655 | A1* | 5/2014 | Mimar | G08B 21/06 348/77 |
| 2015/0360697 | A1* | 12/2015 | Baek | B60W 40/09 701/23 |
| 2015/0367858 | A1* | 12/2015 | Fung | B60Q 9/00 701/1 |
| 2016/0001781 | A1* | 1/2016 | Fung | G16H 50/20 701/36 |
| 2016/0023666 | A1* | 1/2016 | Lee | A61B 5/6893 701/33.4 |
| 2017/0036673 | A1* | 2/2017 | Lee | A61B 3/112 |
| 2017/0267251 | A1* | 9/2017 | Roberts | B60K 28/066 |

FOREIGN PATENT DOCUMENTS

| | | | |
|---|---|---|---|
| KR | 10-2016-0050709 | 5/2016 | |
| KR | 10-2016-0090943 | 8/2016 | |
| WO | WO-2016028228 A1 * | 2/2016 | ......... G06Q 10/0833 |

* cited by examiner

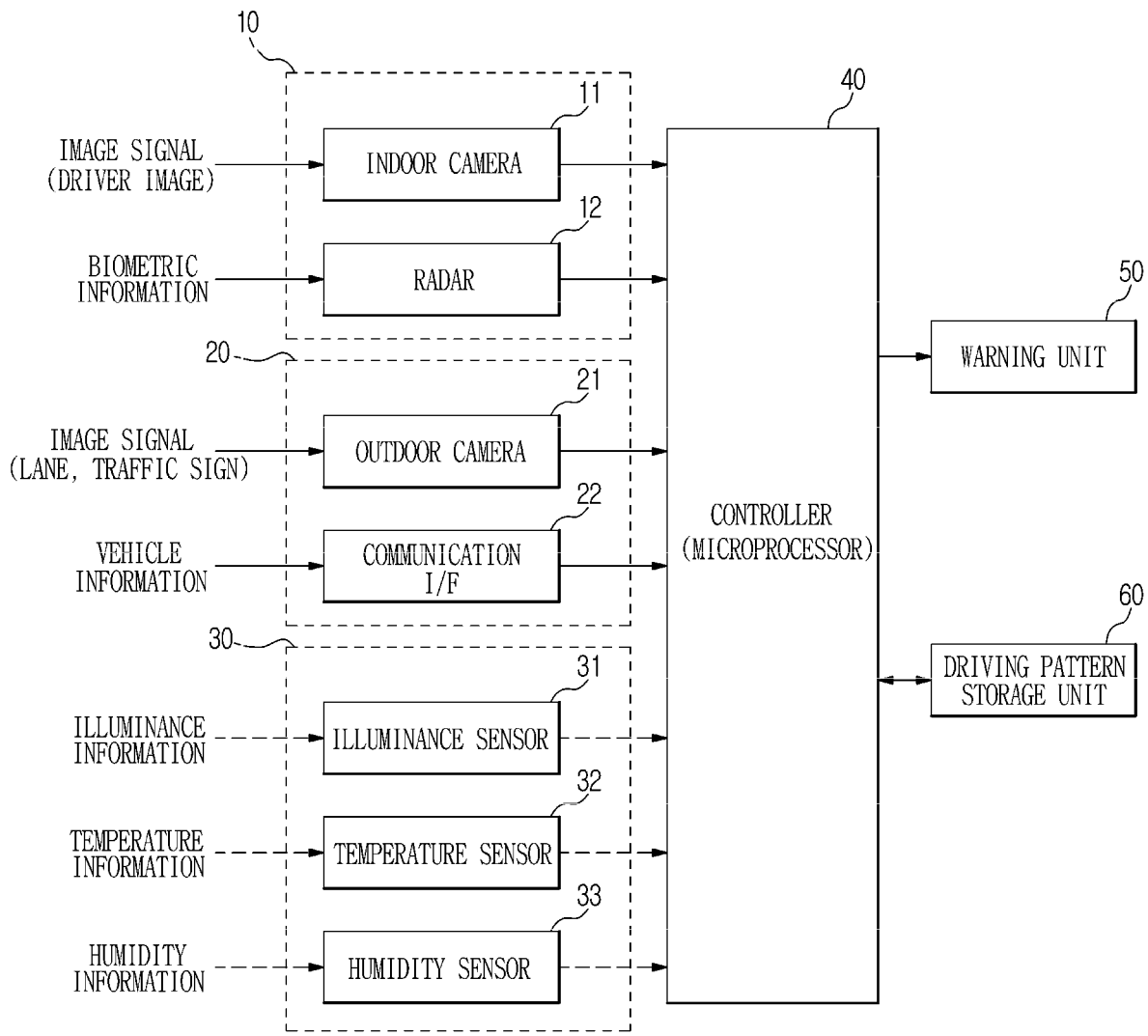

[FIG 2]
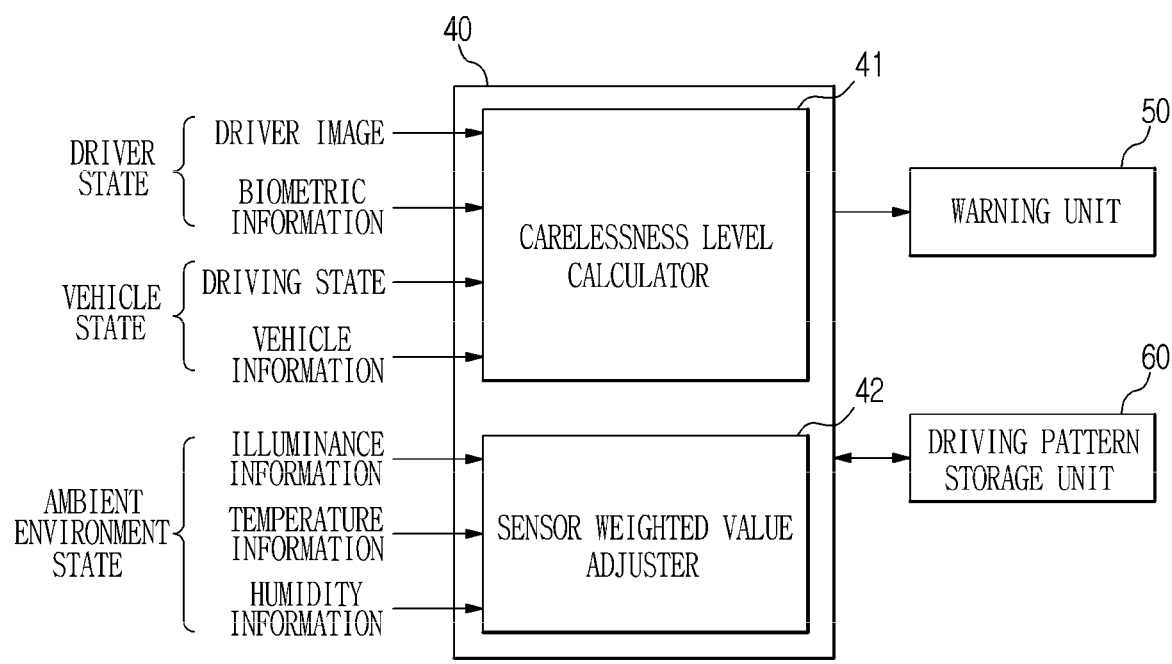

[FIG 3]

| CONDITION | RADAR | INDOOR CAMERA | OUTDOOR CAMERA | COMMUNICATION I/F |
|---|---|---|---|---|
| NORMAL TEMPERATURE & DAYTIME | 0.25 | 0.25 | 0.25 | 0.25 |
| NORMAL TEMPERATURE & NIGHTTIME | 0.4 | 0.1 | 0.1 | 0.4 |
| HIGH TEMPERATURE & DAYTIME | 0.15 | 0.25 | 0.25 | 0.35 |
| HIGH TEMPERATURE & NIGHTTIME | 0.15 | 0.1 | 0.1 | 0.65 |
| LOW TEMPERATURE & DAYTIME | 0.15 | 0.25 | 0.25 | 0.35 |
| LOW TEMPERATURE & NIGHTTIME | 0.15 | 0.1 | 0.1 | 0.65 |

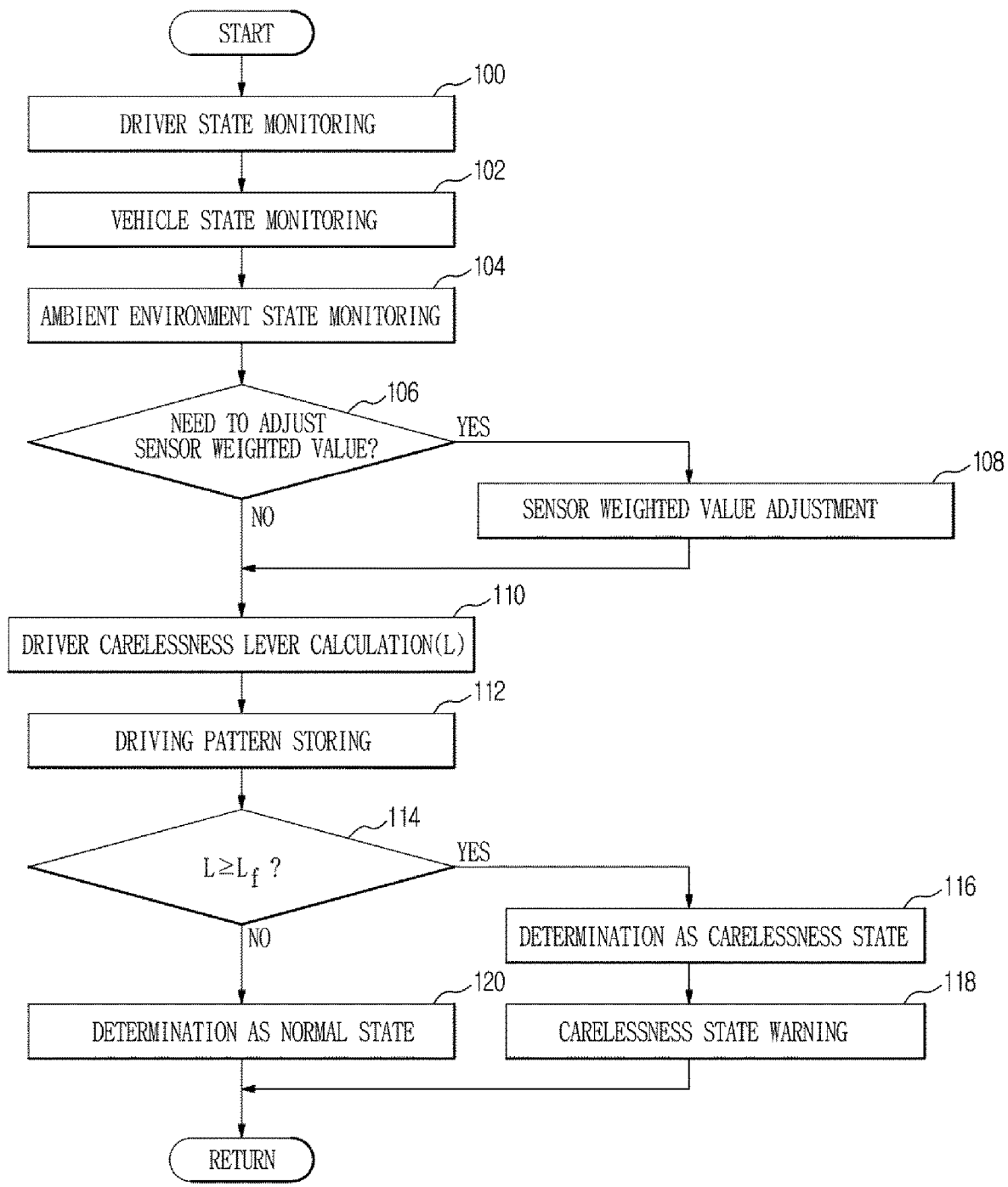

DRIVER STATE MONITORING METHOD AND APPARATUS

CROSS-REFERENCE TO RELATED APPLICATION(S)

This application claims the benefit of Korean Patent Application No. 2017-0030487, filed on Mar. 10, 2017 in the Korean Intellectual Property Office, the disclosure of which is incorporated herein by reference.

BACKGROUND

1. Technical Field

The present disclosure relates to a driver state monitoring method and apparatus, and more particularly to a driver state monitoring method and apparatus for supporting a driver's safe driving.

2. Description of the Related Art

Generally, many people are injured each year because of traffic accidents caused by drowsy driving and carelessness of a driver. In particular, when a driver of a large vehicle such as a bus or a truck causes a car accident due to drowsy driving or carelessness in driving, a great deal of damage may be caused.

Conventionally, a flicker of the eyes through a camera or a heart rate measurement through a heart rate sensing unit is used to determine a driver carelessness state and warn a driver of the driver carelessness state.

In the case of recognizing a pupil in order to determine a driver carelessness state, it is highly influenced by the illuminance inside a vehicle, the lighting condition, or the outside weather.

Further, in the case of recognizing a biological signal such as a heart rate in order to determine a driver carelessness state, it may cost too much due to the addition of separate equipment.

SUMMARY

It is an aspect of the present disclosure to provide a driver state monitoring method and apparatus capable of more accurately and effectively determining a driver carelessness state and warning a driver of the driver carelessness state.

Additional aspects of the present disclosure will be set forth in part in the description which follows and, in part, will be obvious from the description, or may be learned by practice of the disclosure.

In accordance with one aspect of the present disclosure, there may be provided a driver state monitoring apparatus including a driver state sensing unit to sense a driver state, a vehicle state sensing unit to sense a vehicle state, an ambient environment state sensing unit to sense an ambient environment state of the vehicle, a warning unit to warn a driver of a carelessness state, and a controller to assign a weighted value to the driver state sensed through the driver state sensing unit and the vehicle state sensed through the vehicle state sensing unit, respectively, based on the ambient environment state sensed through the ambient environment state sensing unit, calculate a driver carelessness level by applying the assigned respective weighted values, determine whether the driver is in a carelessness state or a normal state based on the calculated driver carelessness level, and warn the driver through the warning unit if the driver is in the carelessness state.

Further, the driver state sensing unit may include an indoor camera to photograph an image of the driver and a radar to measure a heart rate of the driver, the vehicle state sensing unit may include an outdoor camera to photograph a forward image of the vehicle and an communication interface to receive vehicle information through communication with the vehicle, and the controller may include a carelessness level calculator to calculate a driver carelessness level value combining a driver carelessness level value output from the indoor camera, a driver carelessness level value output from the radar, a driver carelessness level value output from the outdoor camera, and a driver carelessness level value output from the communication interface, and a sensor weighted value adjuster to adjust sensor weighted values of the indoor camera, the radar, the outdoor camera and the communication interface, respectively, on the basis of the sensed ambient environment state when the carelessness level calculator calculates the driver carelessness level value.

Further, the driver state monitoring apparatus may further include a look-up table in which the sensor weighted values of the indoor camera, the radar, the outdoor camera, and the communication interface are stored in advance according to the ambient environment state.

In accordance with another aspect of the present disclosure, there may be provided a driver state monitoring apparatus including an indoor camera to photograph an image of a driver, a radar to measure a heart rate of the driver, an outdoor camera to photograph a forward image of a vehicle, a communication interface to receive vehicle information through communication with the vehicle, an ambient environment state sensing unit to sense an ambient environment state of the vehicle, a warning unit to warn a carelessness state of the driver, and a controller to calculate a driver carelessness level value combining a driver carelessness level value output from the indoor camera, a driver carelessness level value output from the radar, a driver carelessness level value output from the outdoor camera, and a driver carelessness level value output from the communication interface, determine whether the driver is in a carelessness state or a normal state based on the calculated driver carelessness level value, and warn the driver through the warning unit if the driver is in the carelessness state, wherein the controller may adjust sensor weighted values of the indoor camera, the radar, the outdoor camera and the communication interface, respectively, on the basis of the sensed ambient environment state when calculating the driver carelessness level value, and calculate the driver carelessness level value by applying the adjusted respective sensor weighted values.

Further, the controller may adjust the sensor weighted values, respectively, using a look-up table in which the sensor weighted values of the indoor camera, the radar, the outdoor camera, and the communication interface are stored in advance according to the ambient environment state.

In accordance with still another aspect of the present disclosure, there may be provided a driver state monitoring method including sensing a state of a driver, sensing a state of a vehicle, sensing an ambient environment state of the vehicle, assigning a weighted value to the sensed driver state and the sensed vehicle state, respectively, based on the sensed ambient environment state, calculating a carelessness level of the driver by applying the assigned respective weighted values, determining whether the driver is in a carelessness state or a normal state based on the calculated driver carelessness level, and warning the driver if the driver is in the carelessness state.

The embodiment of the present disclosure can more accurately and effectively determine and warn a driver state by determining the state of the driver by fusing sensor information monitoring the driver state, sensor information monitoring a vehicle state, and sensor information monitoring a vehicle ambient environment.

The embodiment of the present disclosure can recognize a more accurate driver carelessness state because the sensitivity and reliability degradation of each sensor to the environment can be compensated by adjusting the weighting factor of sensor information according to the importance and priority of information of each sensor based on the ambient environment state.

The embodiment of the present disclosure can detect the sleepiness state and the carelessness state of a driver by using information such as heart rate measurement, lane departure detection, vehicle speed change, and the like even when the driver pupil recognition is impossible.

The embodiment of the present disclosure can warn a driver of the driver carelessness state more quickly, that is, in real time, because the calculation processing is simple by using a look-up table in which the driver carelessness levels are defined in advance.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 1 is a control block diagram of a driver state monitoring apparatus according to an embodiment of the present disclosure;

FIG. 2 is a view for explaining a controller in a driver stare monitoring apparatus according to an embodiment of the present disclosure;

FIG. 3 is an example of a lookup table for adjusting sensor weighted values in the driver state monitoring apparatus according to an embodiment of the present disclosure; and FIG. 4 is a control flow chart of a driver state monitoring apparatus according to an embodiment of the present disclosure.

DETAILED DESCRIPTION

Hereinafter, embodiments of the present disclosure will be described in detail with reference to the accompanying drawings. The following embodiments are provided to fully convey the spirit of the present disclosure to a person having ordinary skill in the art to which the present disclosure belongs. The present disclosure is not limited to the embodiments shown herein but may be embodied in other forms. The drawings are not intended to limit the scope of the present disclosure in any way, and the size of components may be exaggerated for clarity of illustration.

An embodiment of the present disclosure provides a method of calculating a result value indicating a driver carelessness level by fusing the results sensed by each sensor with a single calculation using integrated sensors available in the interior and the exterior of a vehicle and setting a threshold value of the calculated result to more accurately recognize a driver's overall state.

Further, an embodiment of the present disclosure provides a method of easily adjusting the importance and priority of each sensor according to changes in ambient environment such as illuminance, temperature, and humidity, by changing factors in the calculation.

Further, an embodiment of the present disclosure may add or subtract kinds of applicable sensors according to the type of vehicle, the demand for system accuracy, cost, and the like, and may utilize the ambient environment detection sensors (for example, an illuminance sensor, a temperature sensor, and a humidity sensor) mounted on the existing vehicle as they are.

FIG. 1 is a control block diagram of a driver state monitoring apparatus according to an embodiment of the present disclosure.

Referring to FIG. 1, a driver state monitoring apparatus may include a driver state sensing unit 10, a vehicle state sensing unit 20, an ambient environment state sensing unit 30, a controller 40 and a warning unit 50.

The controller 40 is electrically connected to the driver state sensing unit 10, the vehicle state sensing unit 20, the ambient environment state sensing unit 30, and the warning unit 50.

The driver state sensing unit 10 senses a state of a driver. The driver state sensing unit 10 may include an indoor camera 11 and a radar 12.

The indoor camera 11 photographs the driver so as to be able to sense the driver state (blinking eyes, drooping head, etc.).

The indoor camera 11 monitors the driver state by utilizing an RGB image stream, an IR image sensor or the like. At this time, the indoor camera 11 is provided at a position where it can receive the least influence on the rotation of the handle, elongation of the driver, and back and forth position.

The indoor camera 11 transmits the photographed image signal to the controller 40.

The radar 12 radiates a radar signal to the heart and lungs of a driver for biometrics and receives biometric signals (e.g., heartbeat, respiration) reflected from the heart and lungs.

The radar 12 may be provided on the driver's seat closest to the heart and lungs in a straight line.

The radar 12 transmits the received biometric signals to the controller 40.

The driver state sensing unit 10 may include various sensors that can sense the driver state in addition to the indoor camera 11 and the radar 12.

The vehicle state sensing unit 20 senses a state of a vehicle. The vehicle state sensing unit 20 may include an outdoor camera 21 and a communication interface 22. The communication interface 22 may include CAN interface (CAN I/F; Controller Area Network Interface), LIN (Local Interconnect Network), and FlexRay.

The outdoor camera 21 photographs lanes and traffic signs so as to sense the driving state of the vehicle.

The outdoor camera 21 is mounted behind a rearview mirror and photographs the frontward direction in which the vehicle is running.

The outdoor camera 21 transmits the photographed image signal to the controller 40.

The communication interface 22 performs communication with an electronic brake system mounted on the vehicle in accordance with a control signal of the controller 40.

The communication interface 22 receives vehicle information such as vehicle speed and steering change from the electronic brake system.

The communication interface 22 transmits the received vehicle information to the controller 40. For example, the electronic brake system may be an ESC (Electronic Stable Control) system or an ABS (Anti-lock Brake System) which have vehicle information.

The communication interface 22 can receive vehicle information in communication with any system having vehicle information including the vehicle speed and the steering angle in addition to the electronic brake system.

The vehicle state sensing unit 20 may include various sensors and interfaces for sensing a driving state of a vehicle and vehicle information in addition to the outdoor camera 21 and the communication interface 22.

The ambient environment state sensing unit 30 senses an ambient environment state of a vehicle.

The ambient environment state sensing unit 30 may include an illuminance sensor 31, a temperature sensor 32, and a humidity sensor 33.

The illuminance sensor 31 measures the amount of light incident from the outside.

The illuminance sensor 31 is provided on a crash board of a vehicle, and can receive the light incident on the entire region of the surroundings and measure the light amount. The illuminance sensor 31 transmits the measured light amount to the controller 40.

The temperature sensor 32 measures the temperature outside of a vehicle.

The temperature sensor 32 is provided inside a radiator grill of a vehicle and can measure the temperature outside of the vehicle.

The humidity sensor 33 measures the external humidity of a vehicle.

The ambient environment state sensing unit 30 may include various sensors capable of sensing the ambient environment state of a vehicle in addition to the illuminance sensor 31, the temperature sensor 32, and the humidity sensor 33.

The ambient environment state sensing unit 30 is used to increase the reliability of a driver state recognition by sensing the ambient environment state. An illuminance sensor and a temperature sensor mounted on a conventional vehicle may be used.

The warning unit 50 warns the carelessness state of a driver on a screen and/or by voice in accordance with a control signal of the controller 40.

The controller 40 may be composed of a microprocessor.

The controller 40 senses a driver state through the driver's blinking eye, heart rare measurement and the like by using the indoor camera 11 and the radar 12. The driver state sensing output becomes a driver carelessness level value defined in advance in the form of a look-up table (LUT).

The controller 40 acquires and recognizes a driving state of the vehicle and vehicle information by using the outdoor camera 21 and the communication interface 22. The controller 40 recognizes a lane by the outdoor camera 21 and senses the lane departure/driving state (the number of times and the duration). In addition, the controller 40 recognizes speed signs and traffic lights, and recognizes whether or not a regulation speed is complied with and the reaction speed according to the traffic signal change. At this time, the communication interface 22 comprehensively receives information such as vehicle steering change, heading angle of the vehicle, vehicle speed, and the like. The driving state and the vehicle information sensing output become a driver carelessness level value defined in the LUT form in advance.

The controller 40 acquires a vehicle ambient environment state through the ambient environment state sensing unit 30. The controller 40 acquires basic information for variably setting the reliability of each sensor constituting a system in accordance with the change of the ambient environment.

The controller 40 may adjust the sensor weighted value of the respective sensors of the driver state sensing unit 10 and the vehicle state sensing unit 20 on the basis of the ambient environment state sensed through the ambient environment sensing unit 30. For example, the controller 40 can distinguish between day and night through the illuminance sensor 31, and can distinguish between low temperature, middle temperature, and high temperature through the temperature sensor 32. The controller 40 can adjust the sensor weighted values of the indoor camera 11, the radar 12, the outdoor camera 21 and the communication interface 22, respectively, based on the night, day, and temperature, according to the outputs of the illuminance sensor 31 and the temperature sensor 32.

In this way, the controller 40 may more accurately and effectively determine a driver carelessness state by fusing information monitoring a driver state using the indoor camera 11 and the radar 12 and information monitoring a vehicle state using the outdoor camera 21 and the communication interface 22 and by determining the driver carelessness state based on the fused information. That is, the controller 40 fuses information monitoring a driver state and information monitoring a vehicle state, calculates a carelessness level of a driver based on the fused information, determines whether the driver is in a carelessness state or a normal state based on the calculated carelessness level, and warns the driver of the carelessness state through the warning unit 50 when the driver is in an carelessness state.

The controller 40 may monitor an ambient environment state through the ambient environment state sensing unit 30 in the process of determining a carelessness state of the driver, and change the priority and importance of each sensor such as the indoor camera 11, the radar 12, the outdoor camera 21, and the communication interface 22 according to the monitored ambient environment state. The controller 40 can compensate for the sensitivity and reliability degradation of each sensor to the environment by using the ambient environmental state to adjust the sensor weighted value factor.

FIG. 2 is a view for explaining a controller in a driver state monitoring apparatus according to an embodiment of the present disclosure.

Referring to FIG. 2, the controller 40 may include a carelessness level calculator 41 and a sensor weighted value adjuster 42.

The carelessness level calculator 41 fuses the driver carelessness levels output from the sensors 11 and 12 for sensing a driver state and from the sensors 21 and 22 for sensing a vehicle state with one calculation and generates and outputs one output value. For example, by fusing and calculating the respective driver carelessness levels output from the indoor camera 11, the radar 12, the outdoor camera 21 and the communication interface 22, one output value is generated.

The carelessness level calculator 41 calculates a carelessness level by the following equation [1] according to the number of the sensors.

$$\text{Carelessness level}(N) = \alpha \cdot S_1 + \beta \cdot S_2 + \gamma \cdot S_3 + \ldots + \omega \cdot S_n \quad \text{Equation [1]}$$

Where $\alpha, \beta, \gamma, \omega$ are weighted value adjusting factors, and $S_n$ is a carelessness level of each sensor.

The weighted value adjusting factors and the number of the carelessness level outputs of each sensor depend on the number of sensors.

The sensor weighted value adjuster 42 adjusts the weighted values of the respective sensors 11, 12, 21, and 22 used in the calculation of the carelessness level calculator 41.

For example, the controller 40 may adjust the weighted value factors of the sensors according to the importance and priority of the respective sensors on the basis of the measured temperature and day and night through the illuminance sensor 31 and the temperature sensor 32, respectively. Accordingly, weighted values of the respective sensors for calculating the driver carelessness level are calculated. The ratio adjustment is performed by setting the sum of the weighted value adjusting factors of the respective sensors to one.

FIG. 3 is an example of a lookup table for adjusting sensor weighted values in the driver state monitoring apparatus according to an embodiment of the present disclosure.

Referring to FIG. 3, in the case of normal temperature & daytime in the look-up table, the radar, the indoor camera, the outdoor camera, and the communication interface are set to all have the same sensor weighted value.

In the case of normal temperature & nighttime, the sensor weighted values for the radar and the communication interface are set relatively high compared to the indoor and outdoor cameras.

In the case of high temperature & daytime, the sensor weighted value for the communication interface is set to the highest and the sensor weighted value for the radar is set to the lowest.

In the case of high temperature & nighttime, the sensor weighted value for the communication interface is set to the highest and the sensor weighted values for the indoor camera and the outdoor camera are set to the lowest.

In the case of low temperature & daytime, the sensor weighted values for the respective sensors are set equal to the case of high temperature & daytime.

In the case of low temperature & nighttime, the sensor weighted values for the respective sensors are set equal to the case of high temperature & nighttime.

In the case of nighttime, since the reliability of the camera recognition result is low, the weighted values of the indoor camera and the outdoor camera are set low and the importance of the vehicle state information received from the radar and the communication interface is set high.

Referring back to FIG. 2, the controller 40 checks whether the carelessness level value output from the carelessness level calculator 41 has a value equal to or greater than a preset value (threshold value). If the carelessness level value is equal to or greater than a preset value, it may be recognized and determined as a carelessness state. A carelessness state refers to all driver states that may be hazardous to driving, including drowsy driving and neglect of front gaze.

If it is determined through the driver state recognition process that the driver is in a carelessness state, the controller 40 may warn the driver by outputting a warning through the warning unit 50.

In addition, in the case where a vibration device for vibrating the steering wheel or the seat is mounted, the controller 40 may call attention to the driver by vibrating the steering wheel or the seat by operating the vibration device.

In addition, the controller 40 may open the window by operating the window device, thereby supporting the driver to get out of the carelessness state.

Meanwhile, the driver state monitoring apparatus may include a driving pattern storage unit 60.

The driving pattern storage unit 60 stores a driver carelessness level calculated by the controller 40.

In the driving pattern storage unit 60, the driver carelessness level values are stored in units of time in association with the driving patterns of the driver. Accordingly, it is possible to provide a logging service capable of improving careless driving habits by allowing the user to confirm the inadequate driving patterns or the like for each time zone on a monitor connected to the driver state monitoring apparatus.

FIG. 4 is a control flow chart of a driver state monitoring apparatus according to an embodiment of the present disclosure.

Referring to FIG. 4, first, the controller 40 monitors a driver state using the indoor camera 11 and the radar 12 (100).

The controller 40 monitors a vehicle state using the outdoor camera 21 and the communication interface 22 (102).

The controller 40 monitors an ambient environment state using the illuminance sensor 31 and the temperature sensor 32 (104).

The controller 40 determines whether a sensor weight adjustment is necessary. For example, in the case where the state in which the ambient environment state is normal temperature & daytime is an initial value, by checking the illuminance and the temperature, it may be determined that adjustment of the sensor weighted value is unnecessary in the case of normal temperature & daytime, and otherwise it may be determined that adjustment of the sensor weighted value is necessary.

If the sensor weighted value adjustment is necessary as a result of the determination in operation mode 106, the controller 40 adjusts each sensor weighted value of the radar, the indoor camera, the outdoor camera and the communication interface according to the lookup table based on the illuminance and the temperature (108).

The controller 40 calculates driver carelessness levels by applying each adjusted sensor weighted value (110). That is, the controller 40 applies the adjusted sensor weighted values to the driver carelessness levels output from the indoor camera 11, the radar 12, the outdoor camera 21 and the communication interface 22, respectively, as shown in Equation [1], thereby calculating one driver carelessness level.

Meanwhile, if it is determined in the operation mode 106 that the sensor weighted value adjustment is unnecessary, the controller 40 calculates the driver carelessness level by applying the initial sensor weighted value in operation mode 110. That is, the controller 40 applies the initial sensor weighted values to the driver carelessness levels output from the indoor camera 11, the radar 12, the outdoor camera 21 and the communication interface 22, respectively, as shown in Equation [1], thereby calculating one driver carelessness level.

The controller 40 stores the calculated driver carelessness level in the driving pattern storage unit 60 as a driving pattern of the driver (112).

The controller 40 compares a calculated driver carelessness level L with a preset value Lf to determine whether the calculated driver carelessness level L is equal to or greater than the preset value Lf.

If the calculated driver carelessness level L is equal to or greater than the preset value Lf as a result of the determination in operation mode 114, the controller 40 determines that the driver is in a carelessness slate (116), and warns the driver of the carelessness state through the warning unit 50 (118).

Meanwhile, if the calculated driver carelessness level L is less than the preset value Lf as a result of the determination in the operation mode 114, the controller 40 determines that the driver is in a normal state (120). Next, it returns to a preset routine.

As described above, the embodiment of the present disclosure does not individually process the driver state sensed using the indoor camera and the radar, and the vehicle state sensed through the outdoor camera and the communication interface, and can compensate for the deterioration of the data reliability of the driver state and the vehicle state sensed through the calculation of carelessness level of fusion type. In addition, the embodiment of the present disclosure can reduce the sensitivity and reliability degradation of the environment of each sensor by adjusting the sensor weighted value of each sensor such as the indoor camera, the radar, the outdoor camera, and the communication interface, using the ambient environment state sensed by the illuminance and temperature sensors.

What is claimed is:

1. A driver state monitoring apparatus comprising:
   a driver state sensing unit to sense a driver state;
   a vehicle state sensing unit to sense a vehicle state;
   an ambient environment state sensing unit to sense an ambient environment state of the vehicle;
   a warning unit to warn a driver of a driver carelessness state; and
   a controller to assign a weighted value to the driver state sensed through the driver state sensing unit and the vehicle state sensed through the vehicle state sensing unit, respectively, based on the ambient environment state sensed through the ambient environment state sensing unit, calculate a driver carelessness level value by combining a driver carelessness level value output from an indoor camera, a driver carelessness level value output from a radar, a driver carelessness level value output from an outdoor camera, and a driver carelessness level value output from a communication interface and applying the assigned respective weighted values, determine whether the driver is in a carelessness state or a normal state based on the calculated driver carelessness level, and warn the driver through the warning unit if the driver is in the carelessness state,
   wherein the controller adjusts sensor weighted values of the indoor camera, the radar, the outdoor camera and the communication interface, respectively, on the basis of the sensed ambient environment state when calculating the driver carelessness level value, and calculates the driver carelessness level value by applying the adjusted respective sensor weighted values.

2. The driver state monitoring apparatus according to claim 1, further comprising: a look-up table in which the sensor weighted values of the indoor camera, the radar, the outdoor camera, and the communication interface are stored in advance according to the ambient environment state.

3. A driver state monitoring apparatus comprising:
   an indoor camera to photograph an image of a driver;
   a radar to measure a heart rate of the driver;
   an outdoor camera to photograph a forward image of a vehicle;
   a communication interface to receive vehicle information through communication with the vehicle;
   an ambient environment state sensing unit to sense an ambient environment state of the vehicle;
   a warning unit to warn a driver of a driver carelessness state; and
   a controller to calculate a driver carelessness level value combining a driver carelessness level value output from the indoor camera, a driver carelessness level value output from the radar, a driver carelessness level value output from the outdoor camera, and a driver carelessness level value output from the communication interface, determine whether the driver is in a carelessness state or a normal state based on the calculated driver carelessness level value, and warn the driver through the warning unit if the driver is in the carelessness state,
   wherein the controller adjusts sensor weighted values of the indoor camera, the radar, the outdoor camera and the communication interface, respectively, on the basis of the sensed ambient environment state when calculating the driver carelessness level value, and calculates the driver carelessness level value by applying the adjusted respective sensor weighted values.

4. The driver state monitoring apparatus according to claim 3,
   wherein the controller adjusts the sensor weighted values, respectively, using a look-up table in which the sensor weighted values of the indoor camera, the radar, the outdoor camera, and the communication interface are stored in advance according to the ambient environment state.

5. A driver state monitoring method comprising:
   sensing a state of a driver;
   sensing a state of a vehicle;
   sensing an ambient environment state of the vehicle;
   assigning a weighted value to the sensed driver state and the sensed vehicle state, respectively, based on the sensed ambient environment state;
   calculating a driver carelessness level of the driver by combining a driver carelessness level value output from an indoor camera, a driver carelessness level value output from a radar, a driver carelessness level value output from an outdoor camera, and a driver carelessness level value output from a communication interface and applying the assigned respective weighted values;
   determining whether the driver is in a carelessness state or a normal state based on the calculated driver carelessness level; and
   warning the driver if the driver is in the carelessness state,
   wherein the controller adjusts sensor weighted values of the indoor camera, the radar, the outdoor camera and the communication interface, respectively, on the basis of the sensed ambient environment state when calculating the driver carelessness level value, and calculates the driver carelessness level value by applying the adjusted respective sensor weighted values.

* * * * *